United States Patent [19]

Muniz

[11] Patent Number: 5,148,983
[45] Date of Patent: Sep. 22, 1992

[54] SCENTED SOUVENIR CARD

[76] Inventor: Ralph Muniz, 112 2nd St., #3, Seal Beach, Calif. 90740

[21] Appl. No.: 745,736

[22] Filed: Aug. 16, 1991

[51] Int. Cl.$^5$ ............................................. A61L 9/04
[52] U.S. Cl. ........................................ 239/56; 239/34
[58] Field of Search .............................. 239/34, 53–60

[56] References Cited

U.S. PATENT DOCUMENTS

| | | | |
|---|---|---|---|
| 2,717,174 | 9/1955 | Casanovas | 239/56 |
| 2,958,469 | 11/1960 | Shuster | 239/56 |
| 4,720,409 | 1/1988 | Spector | 239/54 |
| 4,883,692 | 11/1989 | Spector | 239/56 |

FOREIGN PATENT DOCUMENTS 3332525  3/1984  Fed. Rep. of Germany ........ 239/56

*Primary Examiner*—Andres Kashnikow
*Assistant Examiner*—Karen B. Merritt
*Attorney, Agent, or Firm*—Roger A. Marrs

[57] ABSTRACT

A scented card is disclosed herein having a pair of snap-locked pictorial members joined together enclosing a scented carrier therebetween. The members include preformed islands and cavities which are aligned when the members are joined to define a plurality of passageways interconnecting a central cavity holding the scented carrier with peripheral vents along the edge marginal region of the card in order to conduct scent from the carrier exteriorly of the card. Opposite faces of the card are transparent to expose graphic representations or alpha/numeric indicia.

5 Claims, 1 Drawing Sheet

U.S. Patent    Sep. 22, 1992    5,148,983
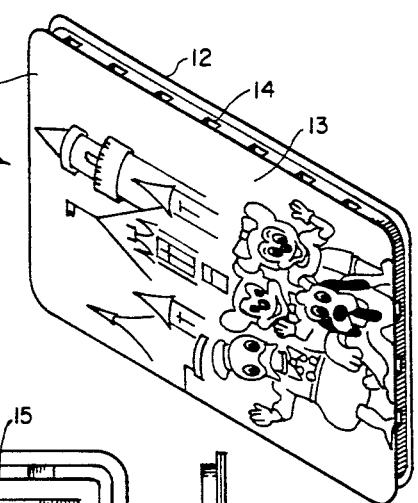
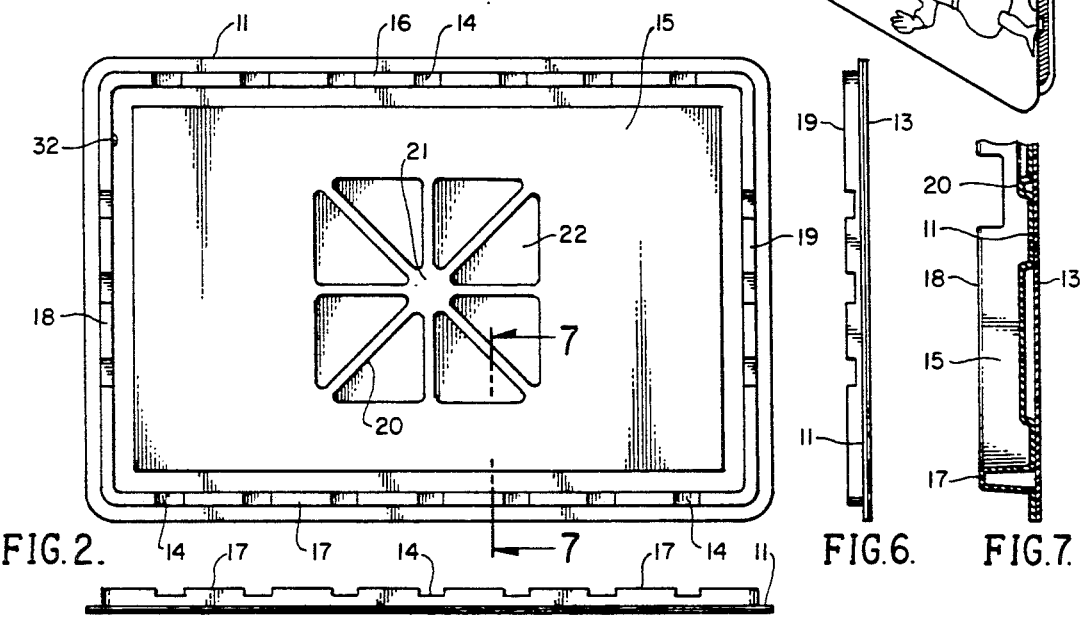
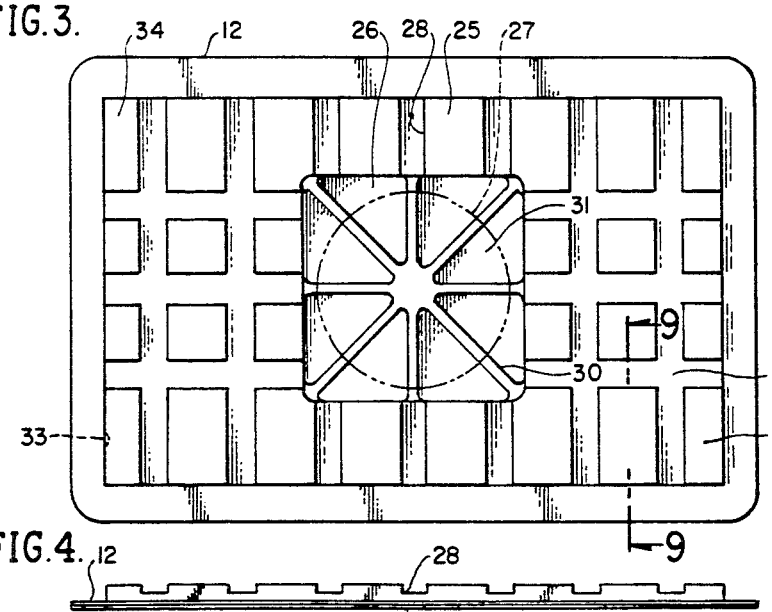
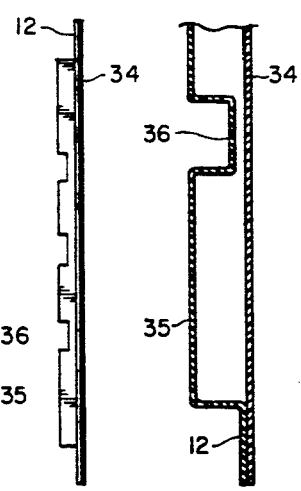

SCENTED SOUVENIR CARD

BACKGROUND OF THE INVENTION

1. Field of the Invention

The present invention relates to the field of souvenir and novelty items and more particularly to a novel souvenir card having means for holding a scented member and additional means for permitting the scent from the member to be exteriorly vented so that the scent complements pictorial representations carried on the opposite faces of the card.

2. Brief Description of the Prior Art

In the past, it has been the conventional practice to employ postcards for communicating good cheer, messages, pictorial subject matter or the like from one person to another, utilizing the postal system. However, problems and difficulties have been encountered when using such conventional postcards which stem largely from the fact that the attention characteristics of the card are limited to the visual aspects and do not pertain to other physical senses No attempt has been made to appeal to the sense of smell, feel or the like. Therefore, the conventional postcard is extremely limited in its attractiveness and novelty characteristics.

Therefore, a long-standing need has existed to provide a mailable card having visual as well as smell attracting characteristics that may be readily introduced into the conventional postal system. Such a novelty item should have a means for holding scented material and for permitting the essence or scent of the material to escape and wherein the essence or scent should be associated with the graphic representations or pictorial subject matter carried on the face of the article.

SUMMARY OF THE INVENTION

Accordingly, the above problems and difficulties are obviated by the present invention which provides a novel souvenir card having a pair of pictorial members exposing graphic or alpha/numeric representations on opposite sides of the card, and which provides for a scent-carrying means to be carried between the pair of members which includes a plurality of passageways terminating in peripheral vents arranged along the edge marginal region of the card when the pair of members have been joined. A snap-lock arrangement as well as means for guiding the assembly of the two card members together is provided and the card is of sufficient size, dimension and weight to permit entry into the postal system for delivery. Preferably, the essence of the scent is directly associated with the graphic or pictorial subject matter portrayed on the members and the members include transparent faces so that the graphic or pictorial subject matter is visually available.

Therefore, it is among the primary objects of the present invention to provide a novel souvenir item having pictorial subject matter or graphic representations carried on opposite sides and wherein a scented pad or the like is held in place permitting the essence of scent of the pad to escape through passageways exteriorly of the card.

Still another object of the present invention is to provide a novelty card or souvenir item which directly relates pictorial subject matter and a desired scent which is carried on the same card.

Another object of the present invention is to provide an inexpensive souvenir item having pictorial subject matter or alpha/numeric indicia carried on at least one face and which incorporates means for releasing a scent associated with the subject matter.

Another object of the present invention is to provide a souvenir item having a pair of members which are guided together and snap-locked into a releasable relationship wherein a plurality of islands and cavities internally define a plurality of passageways leading from a central cavity holding scented material to peripheral vents so that the scent is conducted exteriorly of the card.

BRIEF DESCRIPTION OF THE DRAWINGS

The features of the present invention which are believed to be novel are set forth with particularity in the appended claims. The present invention, both as to its organization and manner of operation, together with further objects and advantages thereof, may best be understood with reference to the following description, taken in connection with the accompanying drawings in which:

FIG. 1 is a front perspective view of the novel souvenir card incorporating the present invention;

FIG. 2 is a side elevational view of the underside of a first member used in the card shown in FIG. 1;

FIG. 3 is a side elevational view of the member shown in FIG. 2;

FIG. 4 is an elevational view of the underside of the second member used in the card shown in FIG. 1;

FIG. 5 is a side elevational view of the second member shown in FIG. 4;

FIG. 6 is an end elevational view of the first member shown in FIG. 2;

FIG. 7 is an enlarged fragmentary cross-sectional view of the first member shown in FIG. 2 as taken in the direction of arrows 7—7 thereof;

FIG. 8 is a side elevational view of the second member shown in FIG. 4;

FIG. 9 is an enlarged cross-sectional view of the second member as taken in the direction of arrows 9—9 of FIG. 4.

DESCRIPTION OF THE PREFERRED EMBODIMENT

Referring now in detail to FIG. 1, the novel souvenir card or device of the present invention is illustrated in the general direction of arrow 10 which includes a pair of members which are joined together to form an integral assembly. One member is indicated by numeral 11, while the other member is indicated by numeral 12. Each member includes a transparent surface through which a graphic representation or a pictorial representation is displayed and such a display may be represented by a card having the graphic subject matter thereon The card, including the graphic subject matter, is indicated by numeral 13. It is to be understood that other graphic material may be placed on the member, such as alpha/numeric characters or advertising or other message indicia. Also, it is to be understood that the display area may be on both members and that the graphics or indicia pertain to a specified subject matter The souvenir card 11 further includes an interior having a plurality of peripheral vents, such as vent 14, through which the essence or scent of a given characteristic may be communicated exteriorly into the surrounding environment. Preferably, the scent or essence conducted exteriorly of the device is associated with the subject matter or the indicia carried on the display areas on the members 11 and 12. Such dispersal of the scent augments the association with the graphic or indicia carried on the display area.

Referring now in detail to FIG. 2, it can be seen that member 11 is of a rectangular shape or configuration and that an internal cavity, indicated by numeral 15, is defined between raised sidewalls 16 and 17 which are arranged in fixed parallel spaced-apart relationship and are integrally terminated with endwalls 18 and 19. The sidewalls and endwalls are provided with spaced-apart notches that define the plurality of vents, such as vent 14. In the center of member 11, there is provided a plurality of raised ribs, such as rib 20, and the center ribs radiate outwardly from a central cavity 21. A plurality of triangular cavities, such as cavity 22, are provided between adjacent ones of the plurality of ribs, such as rib 20. Preferably, the member 11 is composed of a transparent material which is thin and flexible.

Referring to FIGS. 2, 6 and 7, it can be seen that the vents, such as vent 14, are formed in the side and endwalls and that the walls are folded over upon themselves so as to provide a hollow cavity internally. The ribs 20 are raised within the cavity 15 a short distance substantially below the height of the sidewalls. It is more clearly seen in FIGS. 6 and 7 that the member 11 carries the card 13 on its outside so that the pictorial or indicia is visible externally. The member 11 supports the graphic or alpha/numeric indicia and the display material may be attached by adhesive or other suitable means.

Referring now in detail to FIG. 3, the second member of the pair is illustrated by numeral 12 and includes a rectangular sheet of transparent material formed with a plurality of raised islands, such as island 25, wherein the islands are arranged in spaced-apart rows and columns so as to provide a plurality of passageways extending from a central storage area represented by numeral 26 outwardly to the periphery of the member 12. Therefore, when the two members 11 and 12 are snapped together so that the plurality of islands fit within the cavity 15, the plurality of passageways will exit at one end with the plurality of vents 14, while the other end of the passageway is in communication with the storage area 26. Situated within the storage area 26 is provided a pad of material which is preferably porous or the like, that holds a quantity of scented substance. The pad is indicated by numeral 27. Therefore, the essence or scent of the substance will permeate the cavity 26 and be exhausted or carried through the passageways, such as passageway 28, for communication exteriorly of the device via the vents, such as vent 14. The cavity 26 includes a plurality of ribs, such as rib 30, that are intended to hold the pad 27 in position in cooperation with ribs 20 carried within the cavity 15 of the member 11. Therefore, when the pair of members are pressed together, the pad will be retained within the cavity against the opposing surfaces of ribs 20 and 30. Adjacent to the ribs 30, there is provided triangular depressions, such as described with respect to member 11 and depression or recess 22.

It is important to note that the overall width of the islands 25 carried on the edge marginal region of the member 12 is intended to fit between the opposing walls of the sidewalls and endwalls carried on member 11 so that the islands will fit into the cavity 15. This is a snap-lock relationship and, if desired, a plurality of detents and notches may be provided. For example, a detent 32 may be provided on the inside wall of 18 and this detent may snap-lock into a recess 33 carried on an island 34 on member 12. The same arrangement may be provided about the periphery of the islands and the opposing surfaces of the sidewalls on the respective members.

Referring now in detail to FIGS. 5, 8 and 9, it can be seen that the member 12 may be provided with a display card similar to the display element 13 carried on number 11. This latter member is indicated by numeral 34 and is adhesively carried on the outside of member 12. In FIG. 9, numeral 35 indicates another island with a passageway 36 defined in cooperation with an adjacent island.

It should be understood that each of the plurality of passageways is defined by the underside of the respective members 11 and 12 in cooperation with the opposing sidewalls of the respective adjacent islands arranged in spaced-apart arrangement. Therefore, it can be seen that the centralized cavity holding the scented pad 27 is in communication exteriorly of the device by means of the passageways and the respective vents.

In view of the foregoing, it can be seen that the novel souvenir device of the present invention provides a means for exhausting a scented substance exteriorly of the device. Inasmuch as the device is substantially hollow with open-ended passageways, the user may readily press in the center of the device which will forcibly urge the scent or substance to expel and discharge through the passageways and the vents. A pictorial subject matter is associated with the type of scent being discharged. For example, a parade of roses may be portrayed on the display surfaces of the device while the scent being discharged would be of a rose scented substance. It is also to be understood that other sizes, shapes and forms of the device may be employed and that the present invention is not limited to rectangular or square shapes.

While particular embodiments of the present invention have been shown and described, it will be obvious to those skilled in the art that changes and modifications may be made without departing from this invention in its broader aspects and, therefore, the aim in the appended claims is to cover all such changes and modifications as fall within the true spirit and scope of this invention.

What is claimed is:
1. A souvenir device comprising:
  a pair of members joined together to define an internal storage cavity between their opposing surfaces;
  graphic indicia carried on at least one exterior face of said joined pair of members;
  a pad carried in said internal storage cavity holding a quantity of a scented substance;
  means internally communicating said scented substance exteriorly of said joined pair of members;
  said communicating means comprises a plurality of open-ended passageways extending between said internal storage cavity and edge marginal regions of said joined pair of members; and
  said plurality of passageways are defined between opposing surfaces of said members and opposing surfaces of a plurality of raised portions carried on a selected one of said members.
2. The invention as defined in Claim 1 wherein:
  said raised portions constitute spaced-apart islands in fixed relationship having top surfaces engageable with the opposing surface of said member opposite to said member carrying said islands.
3. The invention as defined in Claim 2 wherein:

said member opposite to said member provided with said islands includes a continuous sidewall defining a cavity insertably receiving said islands and said sidewall having a plurality of vents at the end of each of said passageways for discharging said scented substance.

4. The invention as defined in Claim 3 including:
raised ribs within said central storage cavity engaging with said pad to retain said pad therein.

5. The invention as defined in Claim 4 including:
snap-lock means releasably coupling said pair of members together.

* * * * *